(12) United States Patent
Lisitza et al.

(10) Patent No.: US 9,289,518 B2
(45) Date of Patent: Mar. 22, 2016

(54) ENHANCED $^{13}$C NMR BY THERMAL MIXING WITH HYPERPOLARIZED $^{129}$XE

(75) Inventors: Natalia V. Lisitza, Brookline, MA (US); Eduard Y. Chekmenev, Nashville, TN (US); Samuel Patz, Chestnut Hill, MA (US)

(73) Assignee: The Brigham and Women's Hospital, Boston, MA (US)

( * ) Notice: Subject to any disclaimer, the term of this patent is extended or adjusted under 35 U.S.C. 154(b) by 1572 days.

(21) Appl. No.: 12/545,637

(22) Filed: Aug. 21, 2009

(65) Prior Publication Data
US 2010/0158810 A1    Jun. 24, 2010

Related U.S. Application Data

(60) Provisional application No. 61/136,267, filed on Aug. 22, 2008.

(51) Int. Cl.
*A61K 49/10*    (2006.01)
*G01R 33/28*    (2006.01)

(52) U.S. Cl.
CPC .............. *A61K 49/10* (2013.01); *G01R 33/282* (2013.01)

(58) Field of Classification Search
CPC .............................. G01R 33/282; A61K 49/10
USPC ......................................................... 424/9.3
See application file for complete search history.

(56) References Cited

U.S. PATENT DOCUMENTS

| | | |
|---|---|---|
| 6,199,385 B1 | 3/2001 | Driehuys et al. |
| 6,278,893 B1 | 8/2001 | Ardenkjaer-Larson et al. |
| 6,426,058 B1 | 7/2002 | Pines et al. |
| 6,453,188 B1 | 9/2002 | Ardenkjaer-Larsen et al. |
| 6,466,814 B1 | 10/2002 | Ardenkjaer-Larsen et al. |
| 6,630,126 B2 | 10/2003 | Driehuys et al. |
| 6,818,202 B2 | 11/2004 | Pines et al. |
| 6,963,199 B2 | 11/2005 | Sato |
| 7,385,395 B2 | 6/2008 | Pines et al. |
| 2001/0009658 A1 | 7/2001 | Driehuys |
| 2006/0173282 A1 | 8/2006 | Ardenkjaer-Larsen et al. |
| 2007/0156046 A1 | 7/2007 | Hasing et al. |
| 2008/0204014 A1 | 8/2008 | Desvaux et al. |

FOREIGN PATENT DOCUMENTS

WO    WO2007136439 A2    11/2007

OTHER PUBLICATIONS

Abragam, et al., Principles of Dynamic Nuclear Polarisation, Rep. Prog. Phys., 1978, 41:395-467.
Albert, et al., Biological Magnetic Resonance Imaging Using Laser-Polarized 129Xe, Nature, 1994, 370:199-201.
Altes, et al., Hyperpolarized 3He MR Lung Ventilation Imaging in Asthmatics: Preliminary Findings, J. Magn. Reson. Imaging, 2001, 13:378-384.
Bhattacharya, et al., Towards Hyperpolarized 13C-succinate Imaging of Brain Cancer, J. Magn. Reson., 2007, 186:150-155.
Bhattacharya, et al., Ultra-Fast Three Dimensional Imaging of Hyperpolarized 13C In Vivo, MAGMA, 2005, 18:245-256.
Bowers, et al., Transformation of Symmetrization Order to Nuclear-Spin Magnetization by Chemical Reaction and Nuclear Magnetic Resonance, Phys. Rev. Lett., 1986, 57:2645-2648.
Bowers, et al., Parahydrogen and Synthesis Allow Dramatically Enhanced Nuclear Alignment, J. Am. Chem. Soc., 1987, 109:5541-5542.
Bowers, et al., Cross Polarization from Laser-Polarized Solid Xenon to 13CO2 by Low-Field Thermal Mixing, Chem. Phys. Lett., 1993, 205:168-170.
Brossel, et al., La detection de la resonance magnetique des niveaux excites: l'effet de depolarisation des radiations de resonance optique et de fluorescence, Comptes Rendus Hebdomadaires Des Seances De L'Academie Des Sciences, 1949, 229:1213-1215.
Chann, et al., 129Xe-Xe Molecular Spin Relaxation, Phys. Rev. Lett, 2002, 88:113201.
Chekmenev, et al., Pasadena Hyperpolarization of Succinic Acid for MRI and NMR Spectroscopy, J. Am. Chem. Soc., 2008, 130:4212-4213.
Cherubini, et al., Hyperpolarising 13C for NMR Studies Using Laser-Polarised 129Xe: SPINOE vs Thermal Mixing, Chem. Phys. Lett., 2003, 371:640-644.
Day, et al., Detecting Tumor Response to Treatment Using Hyperpolarized 13C Magnetic Resonance Imaging and Spectroscopy, Nat. Med., 2007, 13:1382-1387.
Driehuys, et al., High-Volume Production of Laser-Polarized 129Xe, Appl. Phys. Lett., 1996, 69:1668-1670.
Farrar, et al., Temperature-Dependent 13C Relaxation Studies of Small Molecules, J. Am. Chem. Soc., 1972, 94:699-703.
Fitzgerald, et al., Cross-Relaxation in Laser-Polarized Liquid Xenon, Chem. Phys. Lett, 1998, 284:87-92.
Gabellieri, et al., Therapeutic Target Metabolism Observed Using Hyperpolaized 15N Choline, J. Am. Chem. Soc., 2008, 130:4598-4599.
Gallagher, et al., Magnetic Resonance Imaging of pH In Vivo Using Hyperpolarized 13C-Labelled Bicarbonate, Nature, 2008, 453:940-943.

(Continued)

*Primary Examiner* — Michael G Hartley
*Assistant Examiner* — Leah Schlientz
(74) *Attorney, Agent, or Firm* — Quarles & Brady, LLP

(57) ABSTRACT

A method of preparing a hydrogen-containing $^{13}$C compound test sample exhibiting an enhanced $^{13}$C nuclear magnetic resonance (NMR) signal when exposed to a $^{13}$C NMR pulse sequence is disclosed. In the disclosed method, the hydrogen-containing $^{13}$C compound is mixed with hyperpolarized $^{129}$Xe in the gaseous state, and the mixture is subsequently frozen within a magnetic field. The magnetic field strength is then reduced sufficiently so that spin polarization is transferred from the hyperpolarized $^{129}$Xe to the compound. The magnetic field strength is then increased, and the mixture is thawed to obtain the test sample.

18 Claims, 12 Drawing Sheets

(56) References Cited

OTHER PUBLICATIONS

Gatzke, et al., Extraordinarily Slow Nuclear Spin Relaxation in Frozen Laser-Polarized 129Xe, Phys. Rev. Lett., 1993, 70:690-693.

Goldmann, Spin Temperature and Nuclear Magnetic Resonance in Solids, 1970, Oxford at the Clarendon Press, Oxford University Press, Ely House, London.

Goldman, et al., Conversion of a Proton Pair Para Order Into 13C Polarization by rf Irradiation, for Use in MRI, C. R. Physique, 2005, 6:575-581.

Goldman, et al., Hyperpolarization of 13C Through Order Transfer from Parahydrogen: A New Contrast Agent for MRI, Magn. Reson. Imaging, 2005, 23:153-157.

Golman, et al., Metabolic Imaging by Hyperpolarized 13C Magnetic Resonance Imaging for In Vivo Tumor Diagnosis, Cancer Res., 2006, 66:10855-10860.

Grabias, et al., H NMR Study of Natural and Partially Deuterated Ammonium Hexachlorotellurate, Solid State Nucl. Magn. Reson., 1998, 12:37-44.

Napper, Optical Pumping, Rev. Mod. Phys., 1972, 44:169-249.

Hersman, et al., Large Production System for Hyperpolarized 129Xe for Human Lung Imaging Studies, Acad. Radiol., 2008, 15:683-692.

Horsewill, et al., Quantum Tunnelling Aspects of Methyl Group Rotation Studied by NMR, Prog. Nucl. Magn. Reson. Spectrosc., 1999, 35:359-389.

Kauczor, et al., Pulmonary Ventilation Imaged by Magnetic Resonance: At the Doorstep of Clinical Application, Eur. Respir. J., 2001, 17:1008-1023.

Kilian, et al., Dynamic NMR Spectroscopy of Hyperpolarized 129Xe in Human Brain Analyzed by an Uptake Model, Magn. Reson. Med., 2004, 51:843-847.

Kuzma, et al., Fast Nuclear Spin Relaxation in Hyperpolarized Solid 129Xe, Phys. Rev. Lett., 2002, 88:147602.

Mair, et al., Reduced Xenon Diffusion for Quantitative Lung Study—The Role of SF6, NMR Biomed., 2000, 13:229-233.

Mair, et al., 3He Lung Imaging in an Open Access, Very-Low-Field Human Magnetic Resonance Imaging System, Magn. Reson. Med., 2005, 53:745-749.

Moller, et al., MRI of the Lungs Using Hyperpolarized Noble Gases, Magn. Reson. Med., 2002, 47:1029-1051.

Mugler, et al., MR Imaging and Spectroscopy Using Hyperpolarized 129Xe Gas: Preliminary Human Results, Magn. Reson. Med., 1997, 37:809-815.

Moudrakovski, et al., Gas-Phase Nuclear Magnetic Relaxation in 129Xe Revisited, J. Chem. Phys., 2001, 114:2173-2181.

Navon, et al., Enhancement of Solution NMR and MRI with Laser-Polarized Xenon, Science, 1996, 271:1848-1851.

Patz, et al., Hyperpolarized 129Xe MRI: A Viable Functional Lung Imaging Modality?, Eur. J. Radiol., 2007, 64:335-344.

Patz, et al., Human Pulmonary Imaging and Spectroscopy with Hyperpolarized 129Xe at 0.2T, Acad. Radiol., 2008, 15:713-727.

Rizi, et al., MRI of Hyperpolarized 3He Gas in Human Paranasal Sinuses, Magn. Reson. Med., 1998, 39:865-868.

Ruset, et al., Optical Pumping System Design for Large Production of Hyperpolarized 129Xe, Phys. Rev. Lett., 2006, 96:053002.

Ruset, et al., A System for Open-Access 3He Human Lung Imaging at Very Low Field, Concepts in Magn. Reson. Part B (Magn. Reson. Engineering), 2006, 29B:210-221.

Stull, Vapor Pressure of Pure Substances, Organic Compounds, Industrial and Engineering Chemistry, 1947, 39:517-540.

Swanson, et al., Brain MRI with Laser-Polarized 129Xe, Magn. Reson. Med., 1997, 38:695-698.

Walker, et al., Spin-Exchange Optical Pumping of Noble-Gas Nuclei, Rev. Mod. Phys., 1977, 69:629-642.

ium
ENHANCED $^{13}$C NMR BY THERMAL MIXING WITH HYPERPOLARIZED $^{129}$XE

CROSS-REFERENCE TO RELATED APPLICATIONS

This application claims the benefit of U.S. Provisional Application No. 61/136,267, filed on Aug. 22, 2008, which is incorporated by reference herein in its entirety.

STATEMENT REGARDING FEDERALLY SPONSORED RESEARCH AND DEVELOPMENT

Not applicable.

FIELD OF THE INVENTION

The present invention generally to methods for the enhancement of NMR and MRI signals. Specifically, the present invention relates to methods of increasing the sensitivity of $^{13}$C NMR/MRI by polarization enhancement of $^{13}$C nuclei in hydrogen-containing compounds.

BACKGROUND OF THE INVENTION

Carbon is an essential element and intimately involved in nearly all biochemical pathways. Nuclear Magnetic Resonance (NMR) and Magnetic Resonance Imaging (MRI) can be used to noninvasively explore structure and properties of $^{13}$C compounds. Compared to other nuclei, $^{13}$C has large chemical shift dispersion; for example, the $^{13}$C chemical shift range is about 30-fold greater than that of protons. When $^{13}$C enriched compounds are used, the NMR spectrum is simpler to interpret since only the NMR signals originating from the administered compounds and corresponding metabolites are observed.

However, the analytical potential of $^{13}$C NMR has not been exploited to its full capacity because of poor sensitivity. The low sensitivity of $^{13}$C NMR/MRI originates from the inherently low natural abundance (1.1%) and small gyromagnetic ratio, $\gamma^{13}C=\gamma^{1}H/4$. Thus, $^{13}$C nuclear spin polarization (fraction of nuclear spins contributing to MR signal), is only $4\times10^{-6}$ at 4.7 T. For comparison, the polarization produced by optical methods is close to unity.

The low thermal $^{13}$C spin polarization can be enhanced by polarization transfer to carbon from more abundant protons. A number of approaches have been developed to enhance the thermal $^{13}$C polarization by as much as a factor of four. However, the transfer of thermal polarization leads to only a minor improvement and leaves the sensitivity inadequate for the majority of in vivo applications.

An alternative approach to enhance $^{13}$C NMR signal is to create non-thermal polarization, often referred as "hyperpolarization". Hyperpolarization methods include optical pumping of noble gases, PASADENA (Parahydeogen and Synthesis Allow Dramatically Enhanced Nuclear Alignment),[2,3] and DNP (Dynamic Nuclear Polarization)[4,5]. These methods can potentially create a non-thermal polarization close to unity, thereby increasing $^{13}$C NMR signals by factor $10^4$-$10^5$.

The PASADENA effect relies on the molecular addition of para-hydrogen to a double bond in a substrate molecule via catalytic hydrogenation. The spin polarization of adjacent protons can be transferred to $^{13}$C by various methods[6,7]. DNP is based on polarizing nuclear spins in the solid state at cryogenic temperatures and utilizes the transfer of spin polarization from electrons to the nuclear spins. This mechanism requires the presence of unpaired electrons, which are added to the sample as organic free radicals. Both DNP and PASADENA have been shown to be particularly useful for enhancing the signals of some carbon compounds[8].

Despite recent successes of PASADENA[7-11] and DNP,[12-15] these methods have significant limitations. For example, the PASADENA method is limited to unsaturated molecular precursors with the C=C bond that allow molecular addition of para-hydrogen to produce hyperpolarized molecular agents. DNP requires high field magnets, expensive cryogenic equipment, and several tens of minutes to produce hyperpolarized samples. Moreover, DNP and PASADENA utilize toxic chemicals (free radical or catalyst respectively), which require filtration for use in vivo.

The nuclear spin polarization of the noble gases $^{3}$He and $^{129}$Xe can be enhanced by several orders of magnitude (up to a factor of $10^5$) by optical pumping methods. Hyperpolarized noble gases are produced by transferring the angular momentum from a beam of circularly polarized laser light to the atom's nuclear spins via an intermediate alkali metal vapor step[16-20]. Removal of the alkali metal from the hyperpolarized gas is easily accomplished by a simple freeze out, which is a part of polarization procedure. Importantly, this can be accomplished with virtually no loss of polarization. In the case of PASADENA and DNP filtering out toxic substances requires an extra step upon which some polarization losses might occur. Hyperpolarized noble gases are easily administered via inhalation and therefore, have crucial advantage for in vivo applications, most importantly for human studies. Hyperpolarized noble gas MRI has allowed visualization of the sinuses[21], perfusion in the brain[22,23] and the lung[24-32], with main research effort being devoted to the imaging of lung structure and function.

Hyperpolarized $^{129}$Xe can also be used to enhance $^{13}$C polarization by spin polarization-induced nuclear Overhauser effect (SPINOE)[33,34] or low-field thermal mixing (TM).[4,5,45,36] SPINOE is the result of cross-relaxation between hyperpolarized xenon and other nuclear species. The low-field thermal mixing is performed in a frozen mixture of the hyperpolarized xenon and $^{13}$C-containing compound. TM is driven by the dipolar interactions between the nuclear spins and requires a uniform distribution of $^{13}$C spins in a solid $^{129}$Xe matrix. When the applied magnetic field (referred to as a "mixing field") is comparable to the local dipolar fields, nuclear spins equilibrate their polarizations.

Although several attempts to transfer polarization from hyperpolarized $^{129}$Xe to $^{13}$C spins in the solid state by TM have been implemented,[35,36] the measured transfer efficiency has always been substantially lower than that predicted by theory. A major requirement of the transfer techniques is the formation of a homogeneous phase by $^{129}$Xe and $^{13}$C species. As a result, prior methods have been limited to compounds that dissolve well in liquid xenon. Thus, the reported TM studies have all used carbon disulphide ($^{13}$CS$_2$) due to its good solubility in liquid xenon. The majority of biomolecules, however, have poor xenon solubility, which poses a severe limitation for biologically relevant applications. Hence, there is a need for the development of polarization transfer methods that would be effective for use with biologically relevant $^{13}$C containing compounds, particularly those that may be insoluble in xenon liquid.

SUMMARY OF THE INVENTION

The inventors have developed novel methods of enhancing the $^{13}$C NMR signal of hydrogen-containing carbon compounds using a thermal mixing (TM) procedure. The hydrogen-containing carbon compound is mixed with hyperpolarized $^{129}$Xe, and the mixture is frozen within a magnetic field. The magnetic field is then reduced to allow for the exchange of spin polarization between the $^{13}$C nuclei of the carbon compound and the hyperpolarized $^{129}$Xe. After polarization exchange, the magnetic field is raised to its original value and the mixture is thawed.

The inventors have demonstrated that the method induces significant polarization enhancement in 1-$^{13}$C-acetic acid, and believe this to be the first time that polarization transfer has been reported from $^{129}$Xe to $^{13}$C by thermal mixing for a hydrogen-containing molecule of biomedical importance. The invention will be useful in hyperpolarizing a wide range of $^{13}$C enriched compounds for improved NMR signal sensitivity. As many such compounds are important in biomedical and biophysical research using both NMR and MRI, the invention will greatly facilitate such research.

Accordingly, the invention encompasses in a first aspect a method of preparing a hydrogen-containing carbon-13 ($^{13}$C) compound test sample exhibiting an enhanced $^{13}$C nuclear magnetic resonance (NMR) signal when exposed to a $^{13}$C NMR pulse sequence. First, a compound comprising hydrogen and $^{13}$C and hyperpolarized Xenon-129 ($^{129}$Xe) are mixed. The $^{129}$Xe is hyperpolarized by optical pumping. The mixture is subsequently frozen within a magnetic field. In certain embodiments, the mixture is frozen as a thin film. Preferably, the magnetic field within which the mixture is frozen is the fringe filed of a magnet.

Preferably, the compound and hyperpolarized $^{129}$Xe are mixed in the gas phase. In such embodiments, the compound may be in the liquid phase at room temperature and atmospheric pressure, and the compound may be initially provided as a vapor of the liquid phase. In other embodiments, the compound is mixed with hyperpolarized $^{129}$Xe on a chromatographic column.

After the mixture is frozen, the magnetic field strength is reduced sufficiently so that spin polarization is transferred from the hyperpolarized $^{129}$Xe to the compound. The magnetic field strength is then increased, and the mixture is thawed to obtain a test sample exhibiting enhanced $^{13}$C polarization when undergoing NMR analysis. In preferred embodiments, the step of reducing the magnetic field strength sufficiently so that spin polarization is transferred is performed by increasing the field strength of a separate electromagnet that compensates the existing magnetic field, and the step of increasing the magnetic field strength is performed by decreasing the field strength of the separate electromagnet. More preferably, increasing the field strength of the separate electromagnet is accomplished by switching the electromagnetic on, and decreasing the field strength of the separate electromagnet is accomplished by switching the electromagnet off. Preferably, the mixture is thawed by applying a radio frequency pulse to the mixture.

The hydrogen-containing $^{13}$C compound used in the method may have low solubility in liquid xenon. Preferably, the compound used in the method is a compound of biological relevance. More preferably, the compound of biological relevance is chosen from the group consisting of acetic acid, acetate salts, pyruvate salts, and ethanol. Specific preferred $^{13}$C compounds for use in the method include 1-$^{13}$C—AcH (acetic acid), Na-1-$^{13}$C-acetate, and 2-$^{13}$C—EtOH (ethanol), with 1-$^{13}$C—AcH being the most preferred compound.

In a second aspect, the invention encompasses methods for mixing a test sample having one or more hydrogen-containing $^{13}$C compound(s) and subsequently analyzing the test sample. The method is practiced by vaporizing a composition containing one or more compound(s) comprising hydrogen and $^{13}$C and mixing the resulting vapor with hyperpolarized $^{129}$Xe. Preferred hydrogen-containing $^{13}$C compounds for use in the method include compounds of biological relevance and compounds that have low solubility in liquid xenon.

The resulting mixture is then frozen within a magnetic field. The magnetic field strength is reduced sufficiently so that spin polarization is transferred from the hyperpolarized $^{129}$Xe to the compound(s) within the frozen mixture. The magnetic field strength is then increased, and the mixture is thawed to either obtain the test sample directly, or the thawed mixture is further exposed to one or more other substances to obtain a test sample.

To analyze the test sample, a $^{13}$C nuclear magnetic resonance (NMR) pulse sequence is applied to the test sample, and $^{13}$C active nuclei in the test sample are detected. The $^{13}$C active nuclei can be detected by NMR spectroscopy, magnetic resonance imaging, or both.

In a third aspect, the invention encompasses a test composition comprising a hydrogen-containing $^{13}$C compound exhibiting an enhanced $^{13}$C nuclear magnetic resonance (NMR) signal when exposed to a $^{13}$C NMR pulse sequence. The test composition encompasses any test sample resulting from practicing the methods described above. In preferred embodiments, the hydrogen-containing $^{13}$C compound is a compound of biological relevance that has low solubility in liquid xenon.

Other objects, advantages and features of the present invention will become apparent from the following specification taken in conjunction with the accompanying drawings.

DESCRIPTION OF THE PREFERRED EMBODIMENTS

Figure 1A:
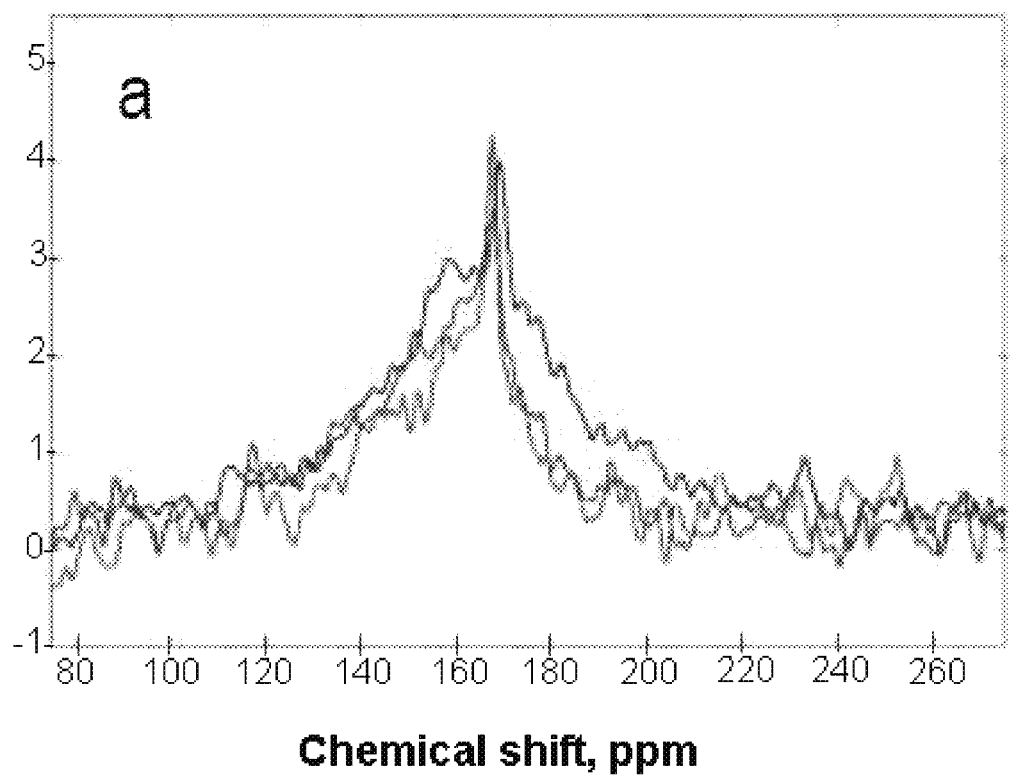
FIG. 1 shows various $^{13}$C NMR spectra of 1-$^{13}$C—AcH taken after exposure to various magnetic fields superimposed onto a control spectra obtained at 4.7 T (the darkest spectrum in all three graphs). A) $^{13}$C NMR spectra of 1-$^{13}$C—AcH obtained after exposure at 500 G for is and 30 s as compared to the spectrum obtained at 4.7 T (upper, darkest line); B) $^{13}$C NMR spectra of 1-$^{13}$C—AcH obtained after exposure at 200 G for is and 30 s as compared to the spectrum obtained at 4.7 T (upper, darkest line); C) $^{13}$C NMR spectra of 1-$^{13}$C—AcH obtained after exposure to zero field for ~1 s, while located at 500 G, 200 G, 100 G, and 50 G as compared to the spectrum obtained at 4.7 T (darkest line). All compared spectra are similar and within expected experimental error as determined by signal/noise ratio.

Unless otherwise defined, all technical and scientific terms used herein have the same meaning as commonly understood by one of ordinary skill in the art to which this invention belongs. Although suitable methods and materials for the practice or testing of the present invention are described below, other methods and materials similar or equivalent to those described herein, which are well known in the art, can also be used.

As used herein, compounds having "biological relevance" include both natural compounds that exist within organisms as reactants, products or intermediates in metabolic or catabolic processes or as having other functions within living organisms. Compounds having biological relevance and artificial compounds that act analogously to such natural compounds. Compounds having biological relevance include without limitation small organic molecules, such as organic acids, esters, acid salts, alcohols, amines, peptides, and monosaccharides; intermediate sized organic molecules such as oligosaccharides, oligopeptides, glycopeptides, and lipids; large organic molecules such as proteins, nucleic acids, glycoproteins and polysaccharides; and inorganic compounds such as sodium bicarbonate. Such compounds also include synthetic compounds having an analogous function in organisms, such as compounds contained in synthetic pharmaceuticals and commercially available blood substitutes.

As used herein, "low solubility in liquid xenon" means having a solubility in liquid xenon that is equal to or less than 10 milliliters of solute per 100 milliliters of xenon.

As used herein, the term "organism" refers to life forms including without limitation animals, plants, microorganisms and fungi. "Organisms" may be either living or dead. The term "organism" also encompasses portions of organisms (e.g., organs, organ group(s), tissue(s), etc.) either in situ or removed from the organism to which they are native.

In a first aspect, the present invention encompasses methods of preparing a hydrogen-containing carbon-13 ($^{13}$C) compound test sample exhibiting an enhanced $^{13}$C nuclear magnetic resonance (NMR) signal when exposed to a $^{13}$C NMR pulse sequence. In the method, a hydrogen-containing $^{13}$C compound is mixed with hyperpolarized $^{129}$Xe. The $^{129}$Xe is hyperpolarized by spin exchange optical pumping. As explained in more detail in Example 3 below, optical pumping is a method for enhancing the spin polarization of gases which consists of irradiating an alkali metal, in the presence of a noble gas, with circularly polarized light. The hyperpolarized gases that result from optical pumping methods have themselves been used for NMR studies of surfaces and for imaging void spaces and surfaces.

In the method of the invention, the hyperpolarized $^{129}$Xe is mixed with the hydrogen-containing $^{13}$C compound. In certain preferred embodiments, both the hyperpolarized $^{129}$Xe and the hydrogen-containing $^{13}$C compound are in the gas phase when mixed. Because both species are in the gas phase, an equilibrium of evenly mixed species can be established without the need for the hydrogen-containing $^{13}$C compound to dissolve in liquid $^{129}$Xe, overcoming the problem of the limited solubility of biological molecules in liquid xenon. Thus, in such preferred embodiments, the hydrogen-containing $^{13}$C compound may have low solubility in liquid xenon.

Many hydrogen-containing $^{13}$C compounds exist as liquids at room temperature and pressure. In order to effectively mix such compounds with gaseous hyperpolarized $^{129}$X, such liquids must be vaporized before they can be mixed. Methods of vaporization include without limitation collecting and removing the vapor present over a volatile liquid, vaporizing a liquid by lowering the ambient pressure, and heating the liquid to increase the vapor pressure of the liquid.

In certain other embodiments, the hydrogen-containing $^{13}$C compound is adsorbed onto a surface of a chromatographic column from an aqueous solution. In such embodiments, the hyperpolarized $^{129}$Xe is then passed trough the column to mix it with the hydrogen-containing $^{13}$C compound. The mixing occurs both on the surface and in the volume of the chromatographic column. After polarization transfer, the hydrogen-containing $^{13}$C compound can be ejected from the column by desorption of the recanting solution. Desorption is accomplished by applying a neutral gas such as nitrogen under a pressure of several atmospheres. Preferred hydrogen-containing $^{13}$C compounds used in this embodiment are water soluble salts, including without limitation pyruvate salts and acetate salts.

Once the hydrogen-containing $^{13}$C compound is mixed with the hyperpolarized $^{129}$Xe and the mixture reaches equilibrium, the mixture is frozen. This step facilitates direct contact between species by means of nonspecific dipolar interactions, and can be applied similarly to a diverse compounds in a similar fashion. The static nature of the dipolar interactions in the solid state facilitates a more efficient polarization transfer than in the liquid phase. In a preferred embodiment, the freezing step is accomplished by exposing the vessel containing the mixture to liquid nitrogen. In certain embodiments, the mixture is frozen as a thin film deposited on a surface.

The freezing process is to be synchronized with the application of an external magnetic field. In certain preferred embodiments, the applied external magnetic field is within the fringe field of a magnet. The magnetic field acts to prevent relaxation processes from occurring within nuclei in the solid state. Following solidification, the magnetic field strength is lowered to the mixing field strength comparable to the local dipolar fields. The lowering of the field strength facilitates the exchange of polarization between the hyperpolarized $^{129}$Xe nuclei and the $^{13}$C nuclei, with the enrichment of the dilute $^{13}$C spins. In certain preferred embodiments, lowering the field strength is accomplished by turning on an electromagnet that works against and thus subtracts from (compensates) the existing magnetic field. After polarization transfer, the external magnetic field strength is increased, preferably back to the original field strength. In certain preferred embodiments, increasing the field strength is accomplished by turning off an electromagnet that works against and thus subtracts from the existing magnetic field.

Finally, the mixture is thawed to obtain a test sample exhibiting enhanced $^{13}$C polarization when undergoing NMR analysis. Preferably, thawing takes place by the application of heat. Heat can be a applied using a number of methods known in the art. Preferably, thawing is accomplished by applying a radio frequency pulse to the mixture. The resulting liquid can then be used for enhanced analysis by conventional $^{13}$C NMR or MRI methods.

Although the method may use any hydrogen-containing $^{13}$C compound, the use of compounds of biological relevance is preferred. Compounds of biological relevance are defined above, and include a variety of compounds. More preferred compounds of biological relevance for use in the method include acetic acid, acetate salts, pyruvate salts, and ethanol, with 1-$^{13}$-C—AcH, Na-1-$^{13}$C-acetate, and 2-$^{13}$C—EtOH being still more preferred. 1-$^{13}$-C—AcH is the most preferred compound for use in the method.

In a second aspect, the invention encompasses methods for mixing a test sample having one or more hydrogen-containing $^{13}$C compound(s) with xenon for use in NMR analysis. The test sample is prepared by mixing a composition in the gaseous phase containing one or more compound(s) comprising hydrogen and $^{13}$C with gaseous hyperpolarized $^{129}$Xe. The composition containing the one or more compound(s) comprising hydrogen and $^{13}$C need not be in the gaseous phase at standard temperature and pressure. In such embodiments, the liquid or solid composition is first vaporized to form a gas, which is then collected and mixed with the gaseous hyperpolarized $^{129}$Xe. Possible vaporization methods that could be used are well known in the art, and such methods are further discussed above.

Although the methods of the invention may use any hydrogen-containing $^{13}$C compound, the use of compounds of biological relevance is preferred. Compounds of biological relevance are defined above, and include a variety of compounds. More preferred compounds of biological relevance for use in the method include acetic acid, acetate salts, pyruvate salts, and ethanol, with 1-$^{13}$-C—AcH, Na-1-$^{13}$C-acetate, and 2-$^{13}$C—EtOH being still more preferred. 1-$^{13}$-C—AcH is the most preferred compound for use in the method. In certain preferred embodiments, the hydrogen-containing $^{13}$C compound has low solubility in xenon liquid.

Once the gaseous mixture reaches equilibrium, the mixture is frozen within a magnetic field. In certain preferred embodiments, the magnetic field within which the mixture is frozen the fringe field of an external magnet. In some embodiments, the freezing step is accomplished by exposing the vessel containing the mixture to liquid nitrogen. In some embodiments, the mixture is frozen as a thin film deposited on a surface.

Once the mixture is frozen, the magnetic field strength is reduced sufficiently so that spin polarization is transferred from the hyperpolarized $^{129}$Xe to the compound(s) within the frozen mixture. In certain preferred embodiments, the reduction of field strength is accomplished by turning on an electromagnet that works against and thus subtracts from (compensates) the existing magnetic field. After spin polarization transfer is complete, the magnetic field strength is increased, preferably back to the original field strength. In some preferred embodiments, increasing the field strength is accomplished by turning off an electromagnet that works against and thus subtracts from the existing magnetic field.

After the magnetic field strength is increased, the mixture is thawed to form a liquid. Thawing takes place by the application of heat. Heat can be applied using a number of methods known in the art. Preferably, thawing is accomplished by applying a radio frequency pulse to the mixture. The thawed mixture is then used for making an NMR test sample.

The thawed mixture may be used directly as a test sample, or it may be exposed to other substances to make up a test sample. The other substances may include conventional solvents known in the art for preparing NMR samples, including without limitation both deuterated solvents such as CDCl$_3$ and aqueous buffer solutions as well as saline solutions and solutions of perfluorocarbon compounds. In some preferred prophetic embodiments, the other substances are all or a portion of an organism, and the thawed mixture is administered to the organism to make the test sample.

The test sample can be analyzed by NMR spectroscopy. Nuclear magnetic resonance (NMR) is a property that magnetic nuclei have in a constant magnetic field under application of the alternating magnetic field at frequency equal to its own frequency. When applied in a constant magnetic field, the alternating magnetic field causes the nuclei to precess, the precession being detected experimentally. The alternating magnetic field is defined as radio frequency (RF) signal. Because of its nuclear spin properties, $^{13}$C isotope nuclei respond to a resonant RF signal. The absorption and emission of the RF signal by the nuclei can be monitored and detected using nuclear magnetic resonance spectroscopy (NMR) or magnetic resonance imaging (MRI) or both. As the skilled artisan would recognize, the $^{13}$C NMR spectrum provides important information regarding the chemical structures contained in a test sample, while MRI provides an accurate image of the test sample.

Accordingly, the methods include the steps of applying a $^{13}$C NMR pulse sequence to the test sample and detecting the $^{13}$C active nuclei in the test sample. In some embodiments, the detection of the $^{13}$C active nuclei is done using NMR spectroscopy. Alternatively, in certain prophetic embodiments, MRI can be use to detect the $^{13}$C active nuclei. In MRI, the absorption and emission signals can be manipulated by additional magnetic fields to build up enough information to construct an image of the sample, where the sample can be a part or all of an organism. Image contrast is created by differences in the strength of the NMR signal recovered from different locations within the sample. These differences depend upon the relative density of excited nuclei, on differences in relaxation times of those nuclei after the pulse sequence, and often on other parameters known by one skilled in the art.

In a third aspect, the invention encompasses the test samples containing one or more hydrogen-containing $^{13}$C compounds exhibiting an enhanced $^{13}$C NMR signal when exposed to a $^{13}$C NMR pulse sequence that are produced by practicing the methods of the invention as described above and in the following Examples. In certain preferred embodiments, the hydrogen-containing $^{13}$C compound contained in the test samples is a compound of biological relevance. It some preferred embodiments, the hydrogen-containing $^{13}$C compound contained in the test samples has low solubility in liquid xenon.

The following Examples are provided as further non-limiting illustrations of particular embodiments of the invention.

EXAMPLES

Example 1

Development and Optimization of Equipment

This Example describes how the inventors constructed and optimized the equipment required for the polarization transfer experiments described in Example 3 below.

The main effort on this part of the project is focused on constructing and optimizing the equipment required for the polarization transfer experiments. In the preliminary experiments with hyperpolarized gas the species are mixed in the gas phase, the acetic acid being chosen as the $^{13}$C-molecule.

The initial step of polarization transfer involves uniform mixing of xenon gas with acetic acid vapor to form the homogeneous phase. A gas line is constructed for gas mixing. The gas line is connected to a bag containing xenon and to a test tube containing acetic acid. The set up is evacuated prior to the gas fill to remove oxygen, an unwanted potential source of $T_1$ relaxation.

The procedure for mixing the species is next developed and optimized. After the species are mixed, the system is transferred to the solid state by cooling with liquid $N_2$. The major requirement is to freeze the system quickly throughout the volume. The rapid and uniform solidification process produces a homogeneous matrix, establishing a dipolar contact between nuclear species.

The solidification is synchronized with the application of the external magnetic field. To accomplish this step experimentally, a cryogenic sample holder and electromagnet are constructed in the lab. The electromagnet is switched on to provide the magnetic field for the initial isolation of species during solidification and freezing. After solidification, the field in the electromagnet is lowered to become comparable to the local dipolar fields and nuclear species exchange their polarizations, with high polarization on $^{13}C$-spins. The system is maintained in the solid state for the period of time sufficient for the polarization transfer to occur (several ms), after which the field is raised to its original value. To accomplish the field cycling on the milli-second time scale, an automated switch is constructed on the basis of commercially available National Instruments Interface Board. The field switching is performed automatically under the LabView control unit, driven by a computer.

After the polarization transfer is accomplished the system is quickly thawed by applying a short, strong rf-pulse. This pulse is provided by an rf-coil designed in the lab. Several different coils are constructed and tested. The major requirement is to thaw the system quickly by depositing heat throughout the volume with rf fields. After polarization transfer is accomplished, the hyperpolarized acetate is analyzed using a double tuned detection coil is constructed for sample analysis.

Example 2

Measurement of $T_1$ Relaxation of $^{129}Xe$ and 1-$^{13}$-C—AcH

This Example describes the inventors' determination of two critical parameters for the successful performance of the polarization transfer experiments described in Example 3: the $T_1$ relaxation times of both xenon-129 and $^{13}C$-acetic acid (1-$^{13}$-C—AcH).

The critical parameters for successful performance of polarization transfer experiments are $T_1$ relaxation times of both xenon and $^{13}C$-acetic acid (1-$^{13}$-C—AcH). These parameters are measured prior to the transfer experiments according to the standard saturation recovery procedure. $T_1$ of xenon gas is found to be 55±3 min, the value being independent of the magnetic field strength (two measurements are performed at 500 G and 5 G respectively). $T_1$ of 1-$^{13}$CAcH is measured to be 35 s and 10 min in liquid and solid states respectively. $T_1$ of hyperpolarized $^{129}Xe$ in gas mixture with 1-$^{13}$C—AcH is determined to be 56±3 min. This value coincides with that for pure xenon gas within experimental error and confirms that there is no polarization loss before solidification. All $T_1$ values agree well with literature data and afford sufficient time for the procedures related to the solidification and melting.

The other critical aspect of polarization transfer experiment is to ensure that no loss of spin polarization of individual species occur in the solid state due to fast $T_1$ relaxation. $T_1$ relaxation in the solid state can be intrinsically fast and further accelerated by exposure of the species to the fringe field as well as the field cycling during the experiment. To explore $T_1$ relaxation of solid 1-$^{13}$-C—AcH the following experiments are performed.

Figure 1B:
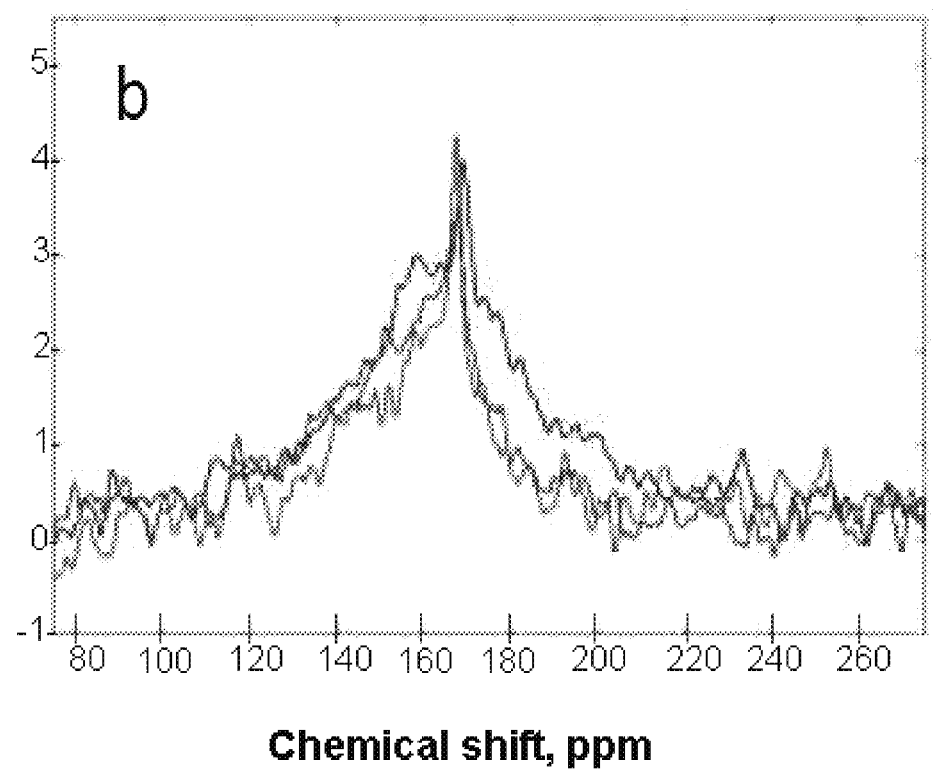
Figure 1C:
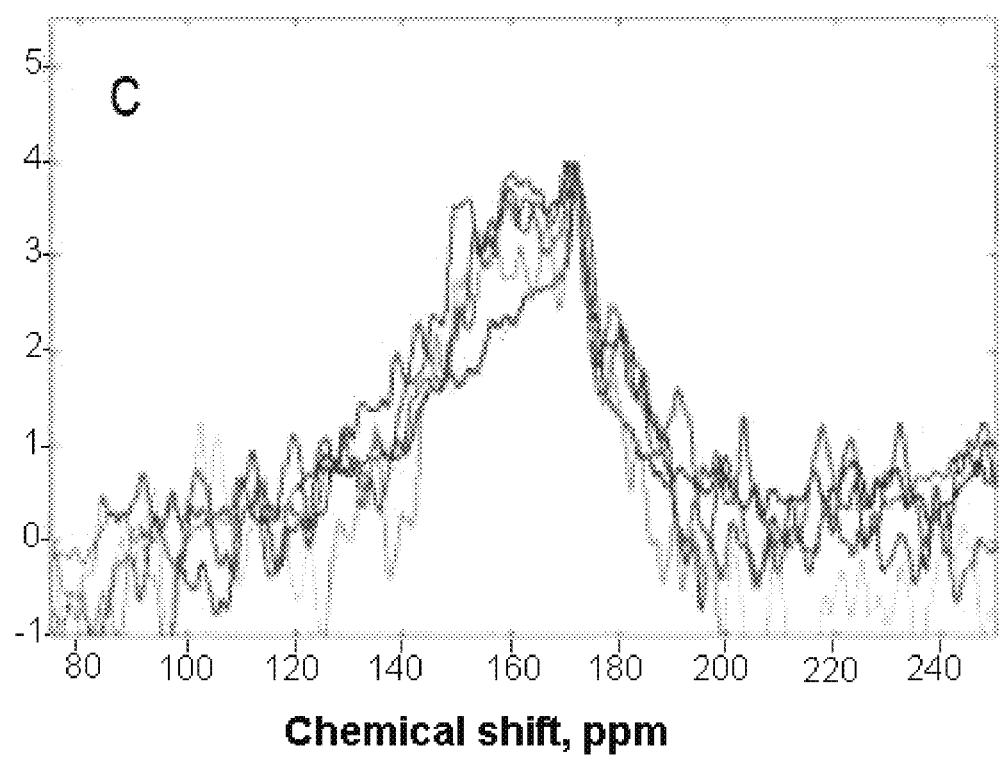

First, the acetic acid is exposed to different fringe fields of a 4.7 T magnet. The goal of these experiments is to find whether the exposure to the fringe field affects $T_1$ relaxation of the acid. Second, the acetic acid is exposed to zero field, while located at different fringe fields of a 4.7 T magnet. The goal of this experiment is to confirm that field cycling does not affects $T_1$ relaxation of the compound. The zero field at the location of the acid sample is created by compensating the fringe field of the 4.7 T magnet with the electromagnet. FIGS. 1a and 1b show the $^{13}C$ NMR spectra of the acetic acid (1-$^{13}$-C—AcH) obtained after exposure at 500 G and 200 G fringe fields as compared to that obtained at 4.7 T. FIG. 1c shows the $^{13}C$ NMR spectra of 1-$^{13}$-C—AcH obtained after exposure to zero field, while located at different fringe fields as compared to that obtained at 4.7 T. All spectra are similar and coincide within the experimental error determined by the S/N ratio. It can be concluded that neither exposure to nor field cycling in the fringe field affect significantly $T_1$ relaxation of the acetic acid.

Example 3

Polarization Transfer Between $^{13}C$ and $^{129}Xe$

In this Example, the inventors demonstrate that the method of the invention can be used successfully to increase the sensitivity of $^{13}C$ NMR/MRI by polarization enhancement of $^{13}C$ nuclei in hydrogen-containing compounds. The specific $^{13}C$ hydrogen-containing compound used in this Example is acetic acid, 1-$^{13}$-C—AcH.

Preliminary Feasibility Study.

Here, we utilize the thermal mixing (TM) procedure to transfer spin polarization from hyperpolarized $^{129}Xe$ to acetic acid 1-$^{13}$CAcH. We mix the two species in the gas phase, after which the mixture is frozen with liquid $N_2$. This approach overcomes the problem of limited $^{13}C$-species solubility in xenon. This report is the first study of the polarization transfer from $^{129}Xe$ to $^{13}C$ achieved by TM for a proton-containing molecule of biological relevance.

The $^{13}C$ NMR polarization was enhanced by 10-fold compared to the equilibrium Boltzmann polarization at 4.7 T. The results presented here show the potential for producing polarization enhanced $^{13}C$ biomarkers for use in biological research and biomedicine.

In the polarization transfer experiment, 1-$^{13}$-C—AcH and isotopically enriched $^{129}Xe$ are mixed in the gas phase. The gas line is evacuated prior to mixing to avoid the presence of oxygen. The gaseous mixture is condensed in liquid $N_2$ at moderate magnetic field. The magnetic field is then cycled to almost zero for several milliseconds. The frozen mixture is delivered to the fringe field of a 4.7 T scanner and the material is thawed. The NMR signal of $^{13}C$ is acquired right after thawing at 4.7 T. The signal of a thermally polarized sample is measured in the 4.7 T field to obtain the equilibrium value of thermal polarization.

Figure 2:
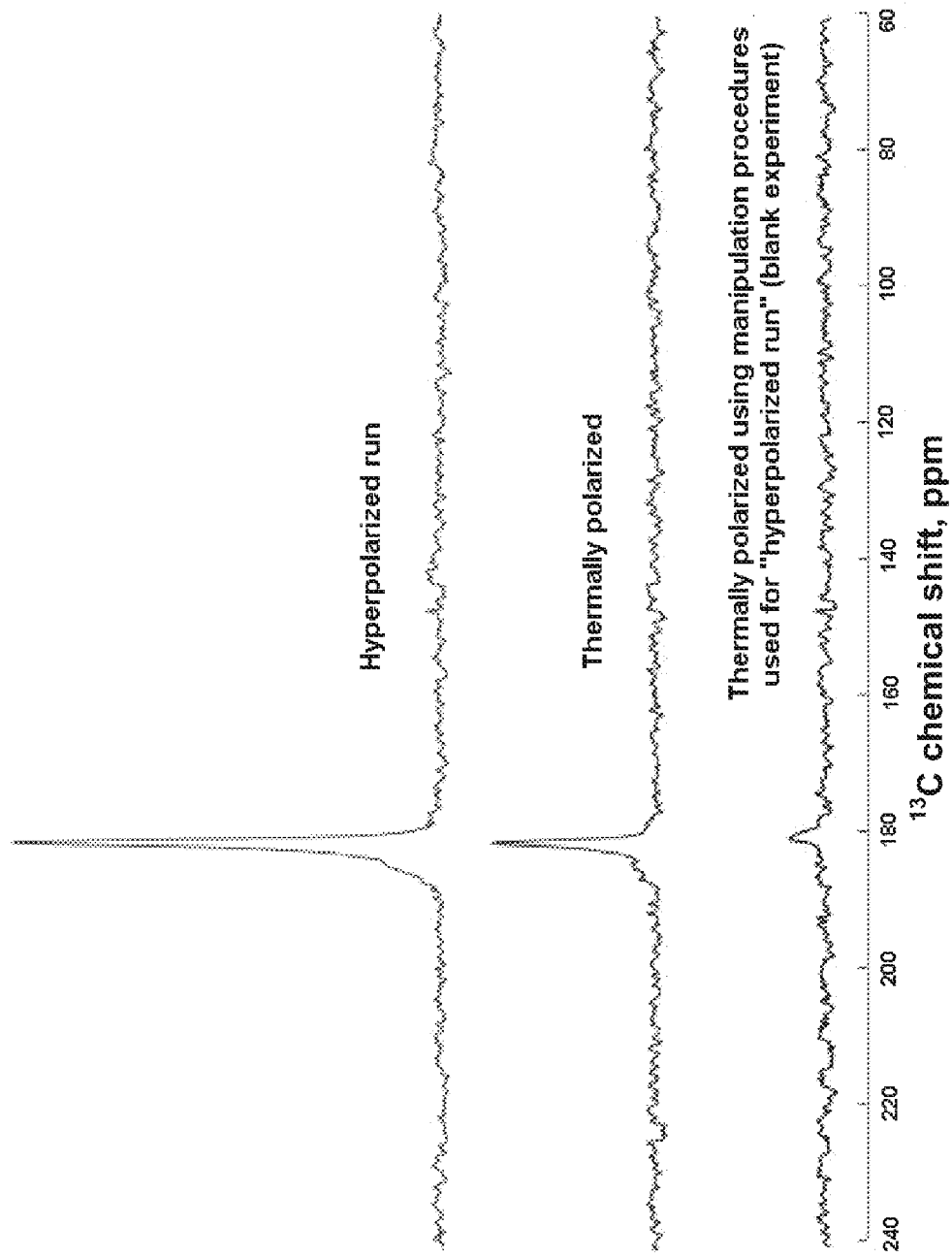
FIG. 2 is an NMR spectrum of $^{13}$C acquired in polarization transfer experiment at 4.7 T (top line), an NMR spectrum of thermally polarized $^{13}$C acquired at the same conditions (middle line), and an NMR spectrum of $^{13}$C acquired in detection experiment only (bottom line).

The results are shown in FIG. 2. The NMR spectrum of the hyperpolarized $^{13}C$ sample acquired right after thawing is shown on top, and the NMR spectrum of the thermally polarized sample is the center line. The enhancement of $^{13}C$ signal by ~3 fold as compared to the thermally polarized sample is detected, with an calculated estimate of initial $^{13}$C-polarization enhancement of 5-10.

This experiment demonstrates that the nuclear spin polarization can be transferred between $^{129}$Xe and $^{13}$C in the solid state by dipolar interactions between the species. However, the enhancement factor observed for $^{13}$C is somewhat lower than the predicted theoretical value. The obtained results indicate that there is a significant polarization loss in the solid state for both 1-$^{13}$-C—AcH and $^{129}$Xe. This implies the cross-relaxation between $^{129}$Xe and $^{131}$Xe in the solid state to be one of the possible reasons responsible for this loss. To minimize the influence of cross-relaxation between xenon isotopes, the $^{129}$Xe and $^{13}$C species should be kept in the high magnetic field prior to the transfer. Exposure to the high magnetic field is known to prevent cross-relaxation in the solid phase.

Materials and Methods.

Hyperpolarized $^{129}$Xe is produced by spin-exchange optical pumping (SEOP), a method originally described by Driehuys et al.[18] and optimized by Ruset et al.[19] A mixture of 1.5% $^{129}$Xe, 25.5% N$_2$ and 73% He (Spectra Gases), at 500 Torr enters a polarizing cell and flows through a spiral with rubidium pools (Alfa Aesar) maintained at 140° C. The Rb vapor is optically pumped with circularly polarized light from a 90 W diode laser array (Coherent). After leaving the optical cell, the gas mixture containing polarized xenon enters a small spiral cell emerged in liquid N$_2$, surrounded by a permanent magnet that provides a holding field of 0.2 T. Here xenon freezes on the cell's walls, while the buffer gases (He and N$_2$) are vacuumed out. A detailed description of the polarizer is given in Reference 19.

Hyperpolarized xenon is transferred to a Tedlar bag (Jensen Inert) and delivered to the facility where the NMR measurements are performed. The delivery is performed using a suitcase equipped with a solenoid coil and fitted with a stainless steel case. This device creates a relatively uniform magnetic field (~30 Gauss) and minimizes the polarization loss during the transfer[37]. The total time between optical pumping and mixing with the acetic acid is ~15 minutes. The polarization of xenon measured at this point varies from 30% to 45% in our experiments.

A critical requirement for the experiment is to perform polarization transfer on the time scale shorter than T$_1$ relaxation of the interacting species. The choice of acetic acid (1-$^{13}$-C—AcH) for the polarization transfer from $^{129}$Xe is determined by the following factors: (i) 1-$^{13}$-C—AcH is involved in important biochemical pathways, (ii) the partial pressure of 1-$^{13}$-C—AcH is sufficiently high to achieve micro-molar concentrations of the compound in the gas phase at normal conditions,[38] and (iii) 1-$^{13}$-C—AcH has a relatively long T1 in solution (~30 s). At the same time, $^{129}$Xe has a T$_1$ of 2.6 hours in the gaseous phase,[39-40] and several minutes in the liquid and solid states in the presence of a modest magnetic field.[41]

Figure 3:
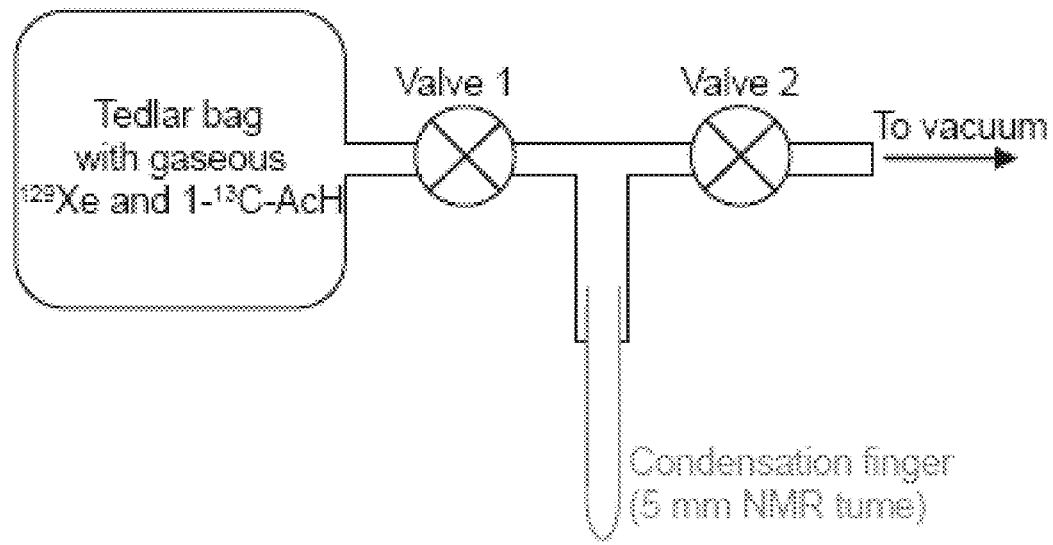
FIG. 3 is a diagram of the apparatus used for condensing the $^{129}$Xe and 1-$^{13}$C—AcH mixture as outlined in Example 3 below.

Prior to TM, the fringe field of the 4.7 T magnet is mapped with a gaussmeter and the locations that correspond to the field strengths of 0.5 T and 0.02 T are identified. These field strengths are used for condensation and field compensation, respectively. Liquid 1-$^{13}$-C—AcH (99% $^{13}$C isotopically enriched, Isotec) is deposited in a Tedlar bag (~50 mg) and evacuated for ~1 minute. A similar bag filled with hyperpolarized xenon is connected to the bag with 1-$^{13}$-C—AcH and ~150 mL of gaseous hyperpolarized $^{129}$Xe is transferred to the bag with the acetic acid. 1-$^{13}$-C—AcH evaporates and is mixed with xenon gas for ~1 minute (see FIG. 3). All parts, connectors, tubing and the condensation finger (a piece of 5 mm NMR tube) shown in FIG. 3 are evacuated for ~5 minutes to a residual pressure of ~1 mTorr prior to the mixing of the compounds to remove the residual oxygen from the system.

At first, valve #1 is opened (see FIG. 3) to deliver the gaseous mixture of 1-$^{13}$-C—AcH and $^{129}$Xe to the condensation finger after which the setup is brought to the fringe field of 0.5 T. The condensation finger, FIG. 3, is subsequently placed in the tightfitted copper tubing and bathed in liquid N$_2$ (see FIG. 4A). Xenon and 1-$^{13}$-C—AcH condense without a visible liquid phase. Copper tubing is used to improve the thermal conductivity between the condensation finger and liquid N$_2$. We refer to the condensation finger inserted into the copper tube as a condensation setup in further discussion. It took 40 s to complete condensation.

The transfer of spin polarization is the most efficient when the mixing field is comparable to the local dipolar fields, the latter varying in the range of several gauss. At this field strength, the T$_1$ relaxation becomes very efficient due to both dipolar and quadrupolar mechanisms[41,42]. The latter occurs because $^{131}$Xe impurities relax the $^{129}$Xe polarization in sufficiently low magnetic fields. Thus, T$_1$ relaxation competes with polarization transfer.

As a compromise, the condensation setup is kept at a magnetic field strength of 0.5 T that exceeds the dipolar and quadrupolar fields by several orders of magnitude during, prior, and after condensation. The mixture is exposed to the mixing field only for a short period of time, required for polarization transfer. The mixing field is generated by compensating the fringe field with a custom-built electromagnet. Because of technical limitations, the maximum compensating field strength is 0.02 T. Consequently, the condensation setup is physically relocated after condensation from 0.5 T to 0.02 T for the polarization transfer.

The condensed sample is collected in a 5 mm NMR tube at the fringe field of 0.5 T and the condensation setup is quickly transferred to a home-built electromagnet situated in the fringe field of 0.02 T (FIG. 4A). The 0.02 T fringe field is compensated by DC electromagnet with the resulting mixing field, B$_{mix}$, ranging from 0.1 mT to 0.5 mT (FIG. 4B). The electromagnet is turned on to maintain B$_{mix}$ for 0.1-0.3 s. The characteristic time required for polarization transfer is proportional to the inverse of the dipolar coupling constant between the spins in the solid-state and is expected to be in 0.1-100 ms range. Thus, our range of B$_{mix}$ is sufficient even for weakly coupled spins to exchange polarizations. We also anticipate B$_{mix}$ to be comparable to the local dipolar fields between $^{129}$Xe, $^{131}$Xe, $^{1}$H, and $^{13}$C spins. The electromagnet switch is controlled by LabView (National Instruments, Austin, Tex.).

Figure 4:
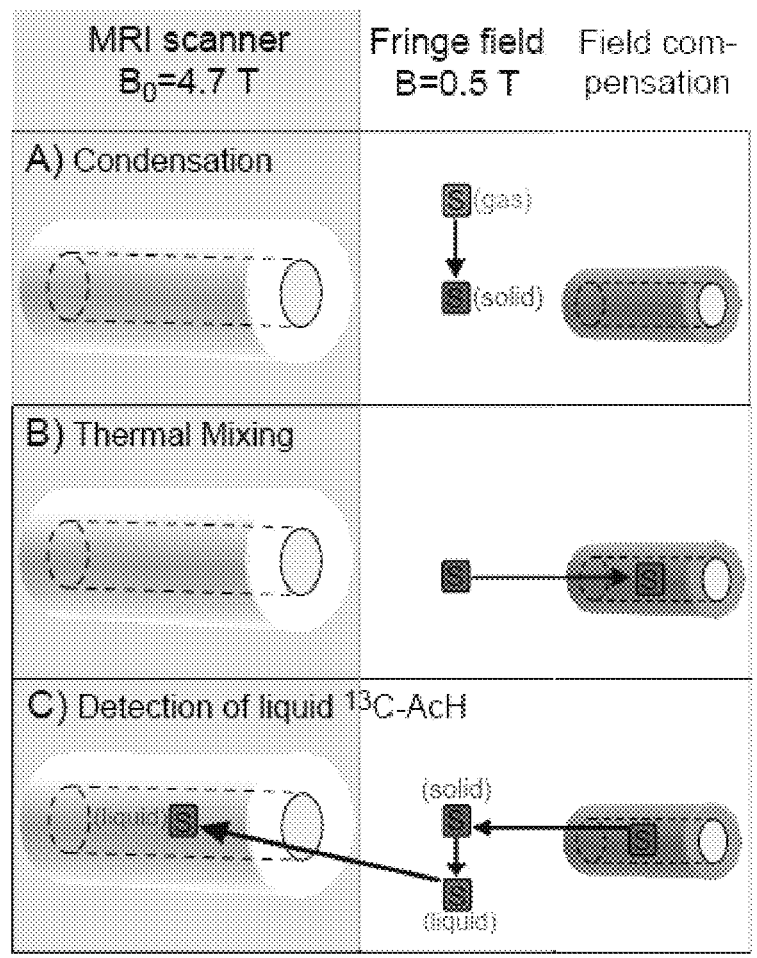
FIG. 4 is a diagram of the experimental setup used for the thermal mixing experiment as outlined in Experiment 1 below: A) the gaseous mixture of 1-$^{13}$C—AcH and $^{129}$Xe is condensed in liquid $N_2$ at 0.5 T; B) quick sample transfer to a field strength of 0.02 T, where TM is performed; C) the setup is transferred back to 0.5 T field, where 1-$^{13}$C—AcH is melted and signal is detected at 4.7 T.
Figure 5:
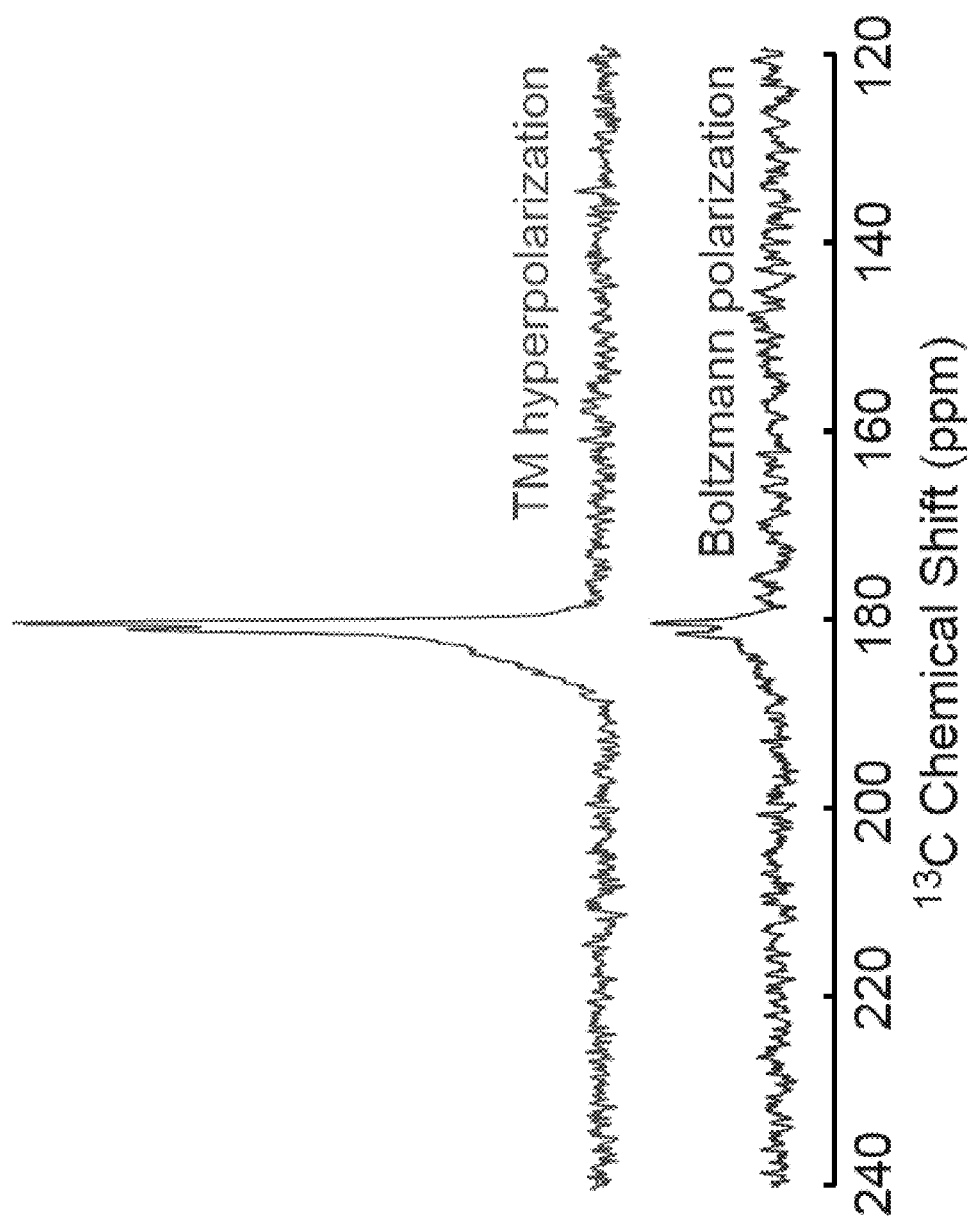
FIG. 5 is a $^{13}$C NMR spectrum of hyperpolarized 1-$^{13}$-C—AcH (top) and a $^{13}$C NMR spectrum from the same sample at equilibrium Boltzmann polarization (bottom). The splitting of the spectral line is likely due to magnetic field inhomogeneities.

Following the TM, the sample is transferred back to the 0.5 T field, where it is thawed for 30-40 s, FIG. 4C. Upon thawing, liquid 1-$^{13}$-C—AcH remains in 5 mm NMR tube, while gaseous xenon expands in the Tedlar bag of the condensation setup, FIG. 4. The $^{13}$C spectrum of liquid hyperpolarized 1-$^{13}$-C—AcH is collected approximately 5-8 s after thawing using a single resonance home-built NMR probe tuned to $^{13}$C resonance frequency (50 MHz). The detected hyperpolarized NMR signal is compared to the thermal signal of the same sample, at 4.7 T, FIG. 5.

Results and Discussion.

The observed enhancement values, expressed as a ratio of integrated signal intensity of the hyperpolarized signal relative to that of the reference thermal spectrum, ranged from 3 to 5, (FIG. 5) depending on the initial xenon polarization (30%-45%), and the $^{129}$Xe:1-$^{13}$-C—AcH molar ratio (the approximate range from 10:1 to 50:1). It should be noted that at least 45 s elapsed between the end of TM and 13C signal detection. Because $^{13}$C T$_1$ is ~30 s in the liquid state as we measured, we estimate that approximately half of the initial polarization is lost due to relaxation. Therefore, the $^{13}$C polarization enhancement factor achieved during TM is extrapolated to ~10. We found no significant dependence of $^{13}$C hyperpolarization on both mixing time (0.1 s to 0.4 s range) and B$_{mix}$, (0.1 mT to 0.5 mT range). In the hyperpolarized $^{129}$Xe/1-$^{13}$-C—AcH matrix with a molar ratio of 1:1 the final carbon polarization is predicted to be about half of the initial xenon polarization. Thus, for a $^{129}$Xe polarization of 30%, the upper limit for the final carbon polarization is 15%, which would correspond to the enhancement factor of about 10$^4$, three orders of magnitude higher than the observed experimental enhancement.

The polarization transfer mechanism in TM is nonselective by its nature and occurs with respect to all nuclear spins that are present in the system including $^1$H, $^{13}$C, and quadrupolar impurities such as $^{131}$Xe. The latter can potentially depolarize $^{129}$Xe, $^{13}$C, and $^1$H in the solid matrix. To determine whether the presence of $^{131}$Xe impurity is the factor that limits the efficiency of our polarization transfer experiment, the polarization of $^{129}$Xe is measured under conditions identical to those in TM procedures. $^{129}$Xe was depolarized from 30% to 10%, which corresponds to T$_1$ relaxation of xenon in the solid state. Therefore, we conclude that quadrupolar impurities are not the dominant source of polarization loss in the solid matrix.

The noteworthy discrepancy between the theoretical limit and the experimental results is likely due to formation of an inhomogeneous solid matrix and/or relaxation processes in the solid state. Since the melting temperatures T$_{melt}$ of $^{129}$Xe and 1-$^{13}$-C—AcH are substantially different (T$_{melt}$=159 K for $^{129}$Xe and T$_{melt}$=290 K for 1-$^{13}$C—AcH), it is conceivable that the acetic acid condenses first, so that the two species become microscopically separated and do not establish the dipolar contact in the solid state. To explore this hypothesis, the condensation is also performed in the mixture of $^{129}$Xe and 1-$^{13}$C-ethanol (10:1 molar ratio). The melting temperature of 1-$^{13}$C-ethanol is T$_{melt}$=170 K, comparable to that of xenon. However, no enhancement of $^{13}$C polarization is observed in TM of 1-$^{13}$C-ethanol. This phenomenon is further explored in Example 4 below. This result suggests that the transfer efficiency of spin polarization is not limited by the species separation in the solid phase.

While the possibility of an inhomogeneous matrix formation cannot be excluded, it is not due to a difference in melting points between 1-$^{13}$-C—AcH and $^{129}$Xe. Aside from quadrupolar interactions with $^{131}$Xe, there are two competing processes of polarization transfer from $^{129}$Xe to $^1$H and $^{13}$C. Protons have ~4 times greater gyromagnetic ratio γ than the $^{13}$C and the internuclear distance between a $^1$H—$^{129}$Xe pair is significantly shorter than that for $^{13}$C—$^{129}$Xe. Since dipolar interactions are proportional to γ and inversely proportional to the cube of the distance between the interacting spins, the couplings of $^{129}$Xe with proton lattice are expected to be about one to two orders of magnitudes greater than those with $^{13}$C. As a result, we anticipate $^{129}$Xe polarization to be transferred to the $^1$H lattice rather than to $^{13}$C. Since the T$_1$ losses of $^{129}$Xe polarization are minimal, we consider other contributions to polarization loss that can occur via $^1$H as well as $^{13}$C spin lattice relaxation processes.

While magnetic fields of <1 mT are necessary for the nuclear spins to exchange polarizations, the dipolar energy reservoir makes the relaxation mechanisms more efficient at low magnetic fields,[42] thereby compromising the net efficiency of the process. For example, $^1$H T$_1$ values in the millisecond range were reported for methyl[43] and ammonium[44] protons at low temperatures and low magnetic field. Such fast relaxation is governed by the dynamics of methyl and ammonium groups. If proton T$_1$ is reduced to the millisecond range, it would result in efficient relaxation of polarization via the $^1$H lattice during TM, thereby explaining the relatively low experimental enhancements of $^{13}$C polarization.

Moreover, cross-polarization from $^{129}$Xe is another viable alternative for polarization transfer to $^{13}$C molecules, albeit with more demanding hardware requirements.

Conclusions.

TM is a useful method to transfer noble gas hyperpolarization via direct dipolar interactions between nuclear species. It does not require sophisticated hardware and can be applied to a wide range of molecules. Moreover, the condensation procedure utilized here does not require dissolving $^{13}$C enriched compounds in liquid xenon and thus, overcomes the problem of limited solubility of biological molecules. We have demonstrated that the $^{13}$C nuclear polarization of 1-$^{13}$-C—AcH can be enhanced by polarization transfer from hyperpolarized $^{129}$Xe in the solid state using TM. The observed experimental maximum enhancement is likely a result of competing polarization transfers from $^{129}$Xe to $^{13}$C and $^1$H and relaxation. The results presented here demonstrate that TM is an experimentally viable approach to enhance $^{13}$C polarization in proton containing molecules.

Example 4

Polarization Transfer Efficiency, Thaw Time, and Phase Separation

In this Example, the inventors determine the dependence of the enhancement factor on thawing time and use 2-$^{13}$C—EtOH in the method of the invention to determine the effect of solid phase species separation on spin polarization transfer efficiency.

Figure 6A:
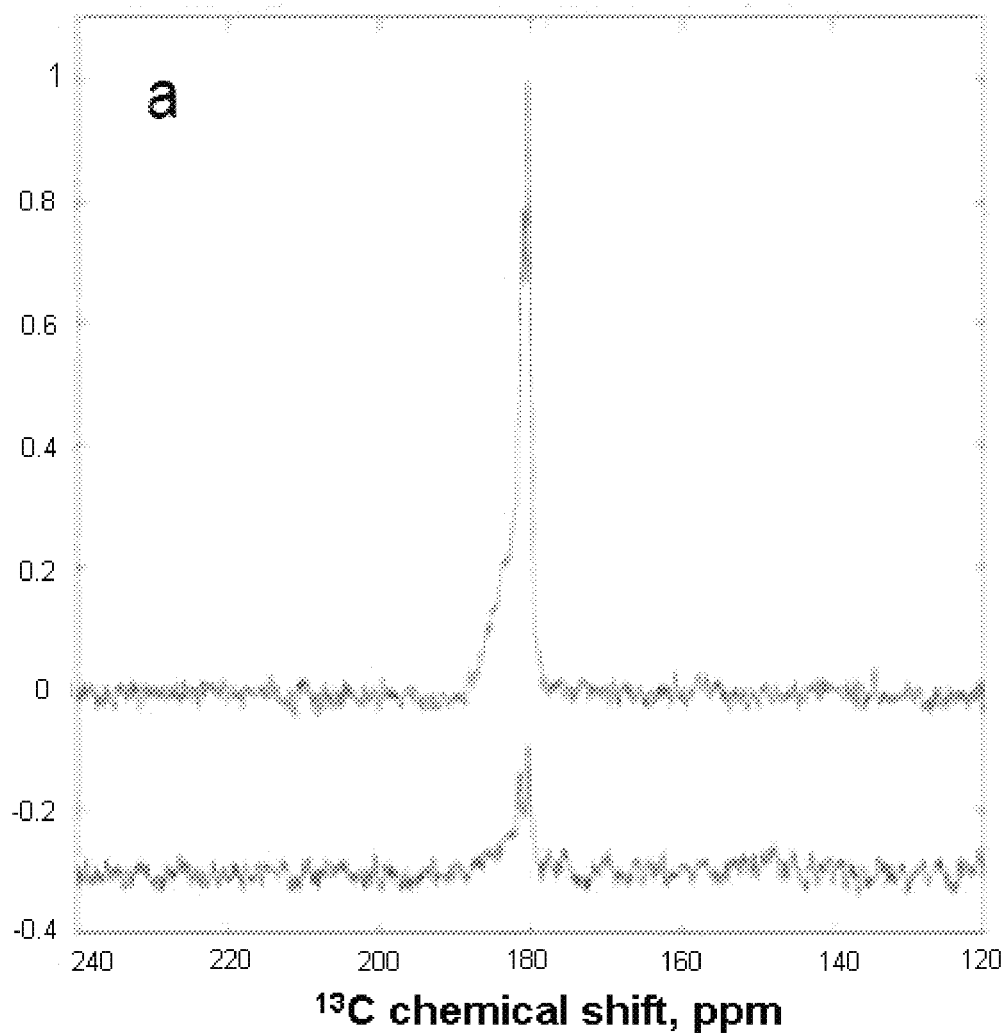
FIG. 6 shows $^{13}$C NMR spectra of hyperpolarized 1-$^{13}$C—AcH (top line) as compared to its thermal spectrum (bottom line) for different thawing times: a) 25 s; b) 35 s; c) 60 s. The corresponding enhancement factors are 5 (a), 3.6 (b), and 1.5 (c).
Figure 6B:
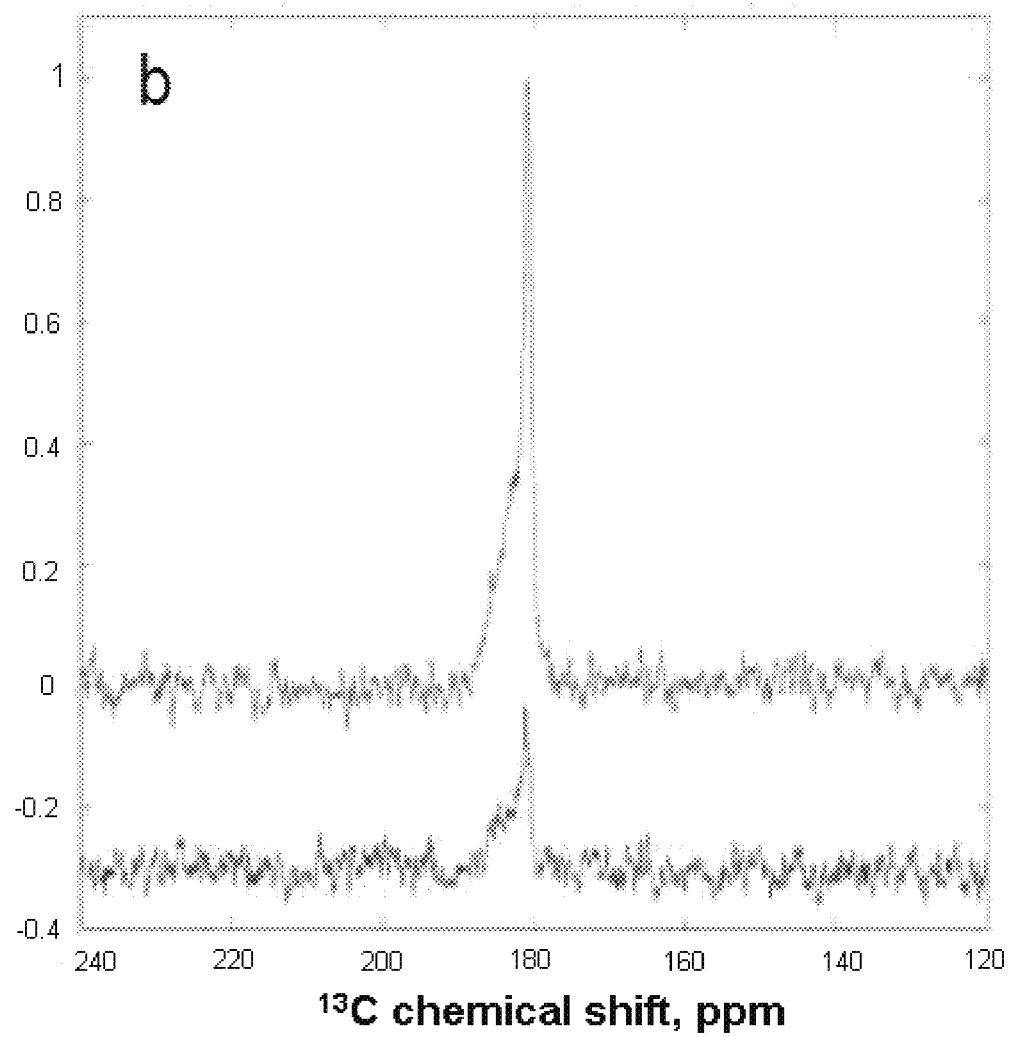
Figure 6C:
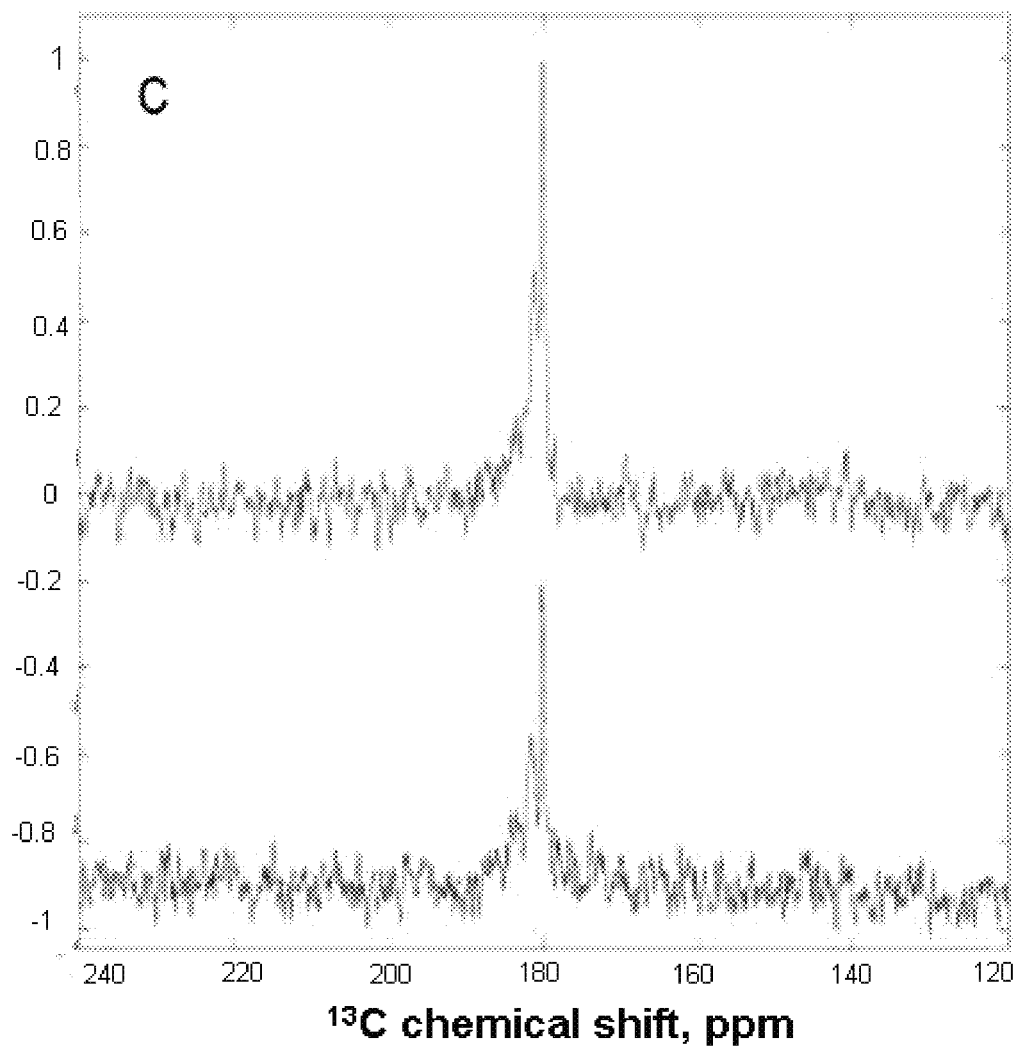

Using the technique outlined in Example 3 above, the inventors measured dependence of the polarization enhancement factor on thawing time for the sample. As shown in FIG. 6, the enhancement factors obtained decrease with increasing thaw time, with a value of 5 at a 25 second thaw time (FIG. 6a), a value of 3.6 at a 35 second thaw time (FIG. 6b), and a value of 1.5 at a 60 second thaw time (FIG. 6c).

Figure 7:
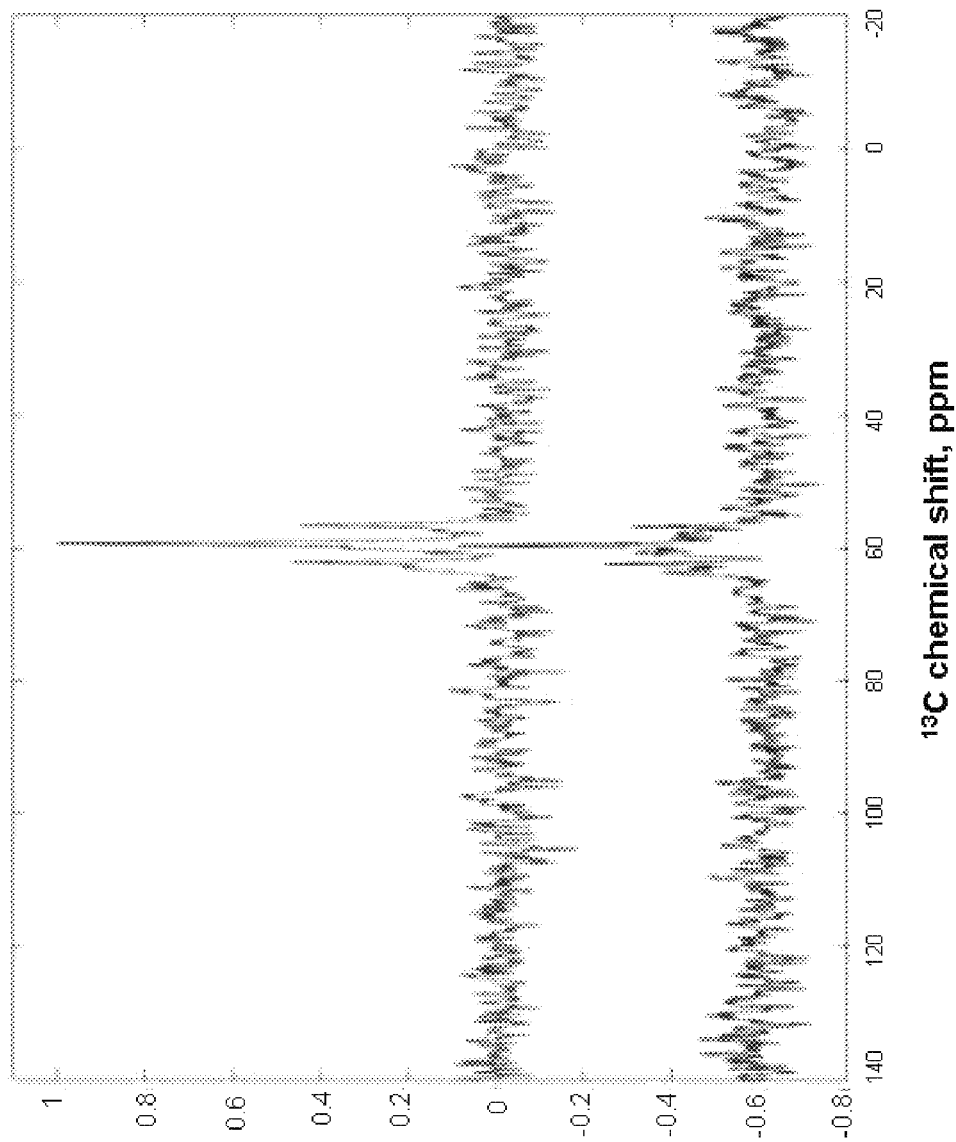
FIG. 7 is a $^{13}$C NMR spectrum of hyperpolarized 2-$^{13}$C—EtOH (top line) as compared to its thermal spectrum (bottom line).

One possible reason for low efficiency of the polarization transfer is that the melting temperatures T$_{melt}$ for $^{129}$Xe and 1-$^{13}$-C—AcH are substantially different (T$_{melt}$=163K for $^{129}$Xe and T$_{melt}$=270K for 1-$^{13}$-C—AcH), so that the acetic acid solidifies first, and the species do not establish the contact in the solid phase. To test this hypothesis, the experiment is performed with 2-$^{13}$C—EtOH as the $^{13}$C-species, following the same procedure as outlined in Example 3 above. EtOH has a melting temperature comparable to that of xenon (T$_{melt}$=170K) and presumably should not form a separate phase upon solidification. FIG. 7 shows the $^{13}$C NMR spectrum of hyperpolarized 2-$^{13}$C—EtOH (top line) as compared to the thermal spectrum (bottom line). The data shows a maximum enhancement factor of 1.2 in this case. This result suggests that the transfer efficiency of spin polarization is not limited by the species separation in the solid phase.

Example 5

Alternative Procedures for Exposing $^{13}$C to $^{129}$Xe

In this prophetic Example, the inventors explain two alternative ways of mixing the $^{13}$C compound and the hyperpolarized $^{129}$Xe for optimal T1 relaxation and polarization transfer: (1) deposition of the $^{13}$C compound from an aqueous solution onto a chromatographic column followed by exposure of the column to hyperpolarized $^{129}$Xe; and (2) solidifying the mixture in a thin layer.

The initial step of the transfer process is to establish contact between $^{129}$Xe and $^{13}$C-compounds. This can be accomplished by either absorption of the $^{13}$C-molecule and $^{129}$Xe on a surface, or mixing $^{13}$C-molecule with xenon in the gas state.

Figure 8:
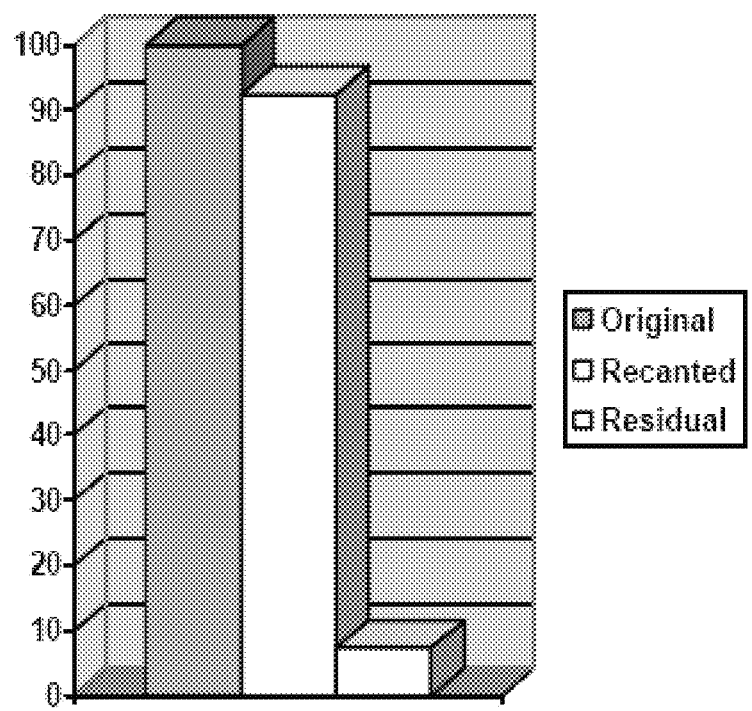
FIG. 8 is a bar graph showing the percentages of pyruvate in recanted solution (middle column) as compared to original solution (leftmost column). The label "residual" (rightmost column) refers to the pyruvate retained on the chromatographic column.

The research conducted in regards to absorption of the $^{13}$C-molecule and $^{129}$Xe on a surface is focused on finding efficient absorbents and optimizing the experimental conditions for deposition and removal of the $^{13}$C-compound. Pyruvate is chosen as $^{13}$C-containing molecule. Our preliminary results demonstrate efficient adsorption of pyruvate on a surface with subsequent desorption into aqueous solution is plausible on a time scale short compared to $T_1$ of both $^{129}$Xe and $^{13}$C spins (seconds for adsorption/desorption vs. minutes for $T_1$ relaxation). It was found that pyruvate can be reversibly deposited from aqueous solution onto a commercially available chromatographic column, the retention molarity being comparable to the cell concentrations (40 μM). The adsorbed pyruvate can be subsequently ejected from the column in several seconds by applying a neutral gas (nitrogen) under pressure of several atmospheres, the recanting solution containing 92.5% of initially deposited pyruvate (FIG. 8).

The materials (the adsorbent and the eluent) as well as the experimental conditions (pH, applied gas pressure) for pyruvate deposition and extraction were found and optimized. To deliver the eluent to the column at high speed, an automated mixer was constructed. The delivery is performed automatically under a LabView control unit, which moves the fluid with gated gas pressures through a series of solenoid valves. The remaining step of the project is to expose the column with deposited pyruvate to hyperpolarized Xe.

There exist two possible sources of fast relaxation in the solid phase. First, when the species form the solid phase, the resulting structure is highly non-uniform because of the spontaneous solidification process. As a consequence, the gradients of the magnetic fields might appear inside the solid mixture due to susceptibility variations, structural defects (vacancies and dislocations etc). The internal gradients accelerate $T_1$ relaxation, giving rising to a significant polarization losses. Second, the system undergoes phase transition upon thawing; $T_1$ relaxation time of xenon at phase transition might become as short as several milliseconds. Under such conditions, relaxation compete with the polarization transfer and a significant fraction of $^{129}$Xe polarization (and potentially, the enhanced $^{13}$C polarization) will be lost before the detection point.

A possible solution to overcome these limitations is to solidify the mixture of $^{129}$Xe and $^{13}$C-compound in a thin layer to minimize the influence of the internal gradients and phase transition. Toward to this goal, a solidification set up was constructed in the laboratory. The set up includes a spiral glass tube within an outer glass cylinder, as in a typical distillation apparatus condenser. The gas mixture is deposited in the internal spiral, while the coolant (such as liquid $N_2$) is supplied to the surrounding cylinder. As it is cooled, the gas mixture solidifies onto the internal glass spiral surface as a thin film within which polarization transfer may occur.

While the present invention has been described in what is perceived to be the most practical and preferred embodiments and Examples, it is to be understood that the invention is not intended to be limited to the specific embodiments set forth above. Further, it is recognized that modifications may be made by one of skill in the art of the invention without departing from the spirit or intent of the invention and, therefore, the invention is to be taken as including all reasonable equivalents to the subject matter of the appended claims. All references cited herein are incorporated by reference for all purposes.

REFERENCES CITED (1) Brossel et al., Comptes Rendus Hebdomadaires Des Seances De L Academie Des Sciences 1949, 229, 1213-1215.
(2) Bowers et al., Phys. Rev. Lett. 1986, 57, 2645-2648.
(3) Bowers et al., J. Am. Chem. Soc. 1987, 109, 5541-5542.
(4) Abragam et al., Rep. Prog. Phys. 1978, 41, 395-467.
(5) Goldman, Spin Temperature and Nuclear Magnetic Resonance in Solids Oxford Univ. Press: Oxford, 1970.
(6) Bhattacharya et al., J. Magn. Reson. 2007, 186, 150-155.
(7) Bhattacharya et al., Magn. Reson. Mat. Phys. Biol. Med. 2005, 18, 245-256.
(8) Farrar et al., J. Am. Chem. Soc. 1972, 94, 699-703.
(9) Chekmenev et al., J. Am. Chem. Soc. 2008, 130, 4212-4213.
(10) Goldman et al., Phys. 2005, 6, 575-581.
(11) Goldman et al., Magn. Reson. Imaging 2005, 23, 153-157.
(12) Day et al., Nat. Med. 2007, 13, 1382-1387.
(13) Gabellieri et al., J. Am. Chem. Soc. 2008, 130, 4598-4599.
(14) Gallagher et al., Nature 2008, 453, 940-U973.
(15) Golman et al., Cancer Res. 2006, 66, 10855-10860.
(16) Happer, Rev. Mod. Phys. 1972, 44: 169.
(17) Walker et al., Rev. Mod. Phys. 1977, 69: 629.
(18) Driehuys et al, Phys. Lett. 1996, 69: 1668.
(19) Ruset et al., Phys. Rev. Lett. 96 (2006) 053002.
(20) Ruset et al., Concepts in Magn Reson Part B (Magn Reson Engineering), 29B (2006) 210.
(21) Rizi et al., Magn. Reson. Med. 1998, 39, 865-868.
(22) Swanson et al., Magn. Reson. Med. 1996, 38: 695.
(23) Kilian et al., Magn. Reson. Med. 2004, 51, 843-847.
(24) Mugler et al, Magn. Reson. Med. 1997, 37: 809.
(25) Albert et al., Nature 1994, 370: 199.
(26) Moller et al., Magn. Reson. Med. 2002, 47: 1029.
(27) Patz et al., Eur J Rad, 64 (2007) 334.
(28) Patz et al., Acad. Radiol. 2008, 15, 713-727.
(29) Altes et al., J. Magn. Reson. Imaging 2001, 13, 378-384.
(30) Kauczor et al., Eur. Resp. J. 2001, 17, 1008-1023.
(31) Mair et al., NMR in Biomedicine 13 (2000) 229.
(32) Mair et al., Magn Reson Med, 53 (2005) 745.
(33) Fitzgerald et al., Chem. Phys. Lett. 1998, 284, 87-92.
(34) Navon et al., Science 1996, 271, 1848-1851.
(35) Bowers et al., A. Chem. Phys. Lett. 1993, 205, 168-170.
(36) Cherubini et al., A. Chem. Phys. Lett. 2003, 371, 640-644.
(37) Hersman et al., 6, 2008, Academic Radiology, Vol. 15.
(38) Stull et al., Industrial and Engineering Chemistry 1947, 39, 517-540.
(39) Chann et al., Phys. Rev. Lett. 2002, 88, 113201.
(40) Moudrakovski et al., J. Chem. Phys. 2001, 114, 2173-2181.
(41) Kuzma et al., Phys. Rev. Lett. 2002, 88, 147602.
(42) Gatzke et al., Phys. Rev. Lett. 1993, 70, 690-693.
(43) Horsewill et al., Prog. Nucl. Magn. Reson. Spectrosc. 1999, 35, 359-389.
(44) Grabias et al., Solid State Nucl. Magn. Reson. 1998, 12, 37-44.

We claim:

1. A method of preparing a hydrogen-containing carbon-13 ($^{13}$C) compound test sample exhibiting an enhanced $^{13}$C nuclear magnetic resonance (NMR) signal when exposed to a $^{13}$C NMR pulse sequence comprising the following steps performed in the indicated order:
   (a) mixing a compound comprising hydrogen and $^{13}$C and hyperpolarized Xenon-129 ($^{129}$Xe);
   (b) applying a magnetic field to the resulting mixture;
   (c) freezing the mixture;
   (d) reducing the magnetic field strength sufficiently so that spin polarization is transferred from the hyperpolarized $^{129}$Xe to the compound by increasing the field strength of a separate electromagnet that compensates the existing magnetic field;
   (e) increasing the magnetic field strength by decreasing the field strength of said electromagnet; and
   (f) thawing the mixture to obtain a test sample exhibiting enhanced $^{13}$C polarization when undergoing NMR analysis.

2. The method of claim 1, wherein both the compound and hyperpolarized $^{129}$Xe are mixed in the gas phase.

3. The method of claim 2, wherein the compound is in the liquid phase at room temperature and pressure.

4. The method of claim 3, wherein the compound is in the form of a vapor of the liquid phase.

5. The method of claim 1, wherein the compound has low solubility in liquid xenon.

6. The method of claim 1, wherein the $^{129}$Xe is hyperpolarized by optical pumping.

7. The method of claim 1, wherein the compound is mixed with hyperpolarized $^{129}$Xe on a chromatographic column.

8. The method of claim 1, wherein the mixture is frozen as a thin film.

9. The method of claim 1, wherein the mixture is thawed by applying a radio frequency pulse to the mixture.

10. The method of claim 1, wherein the magnetic field within which the mixture is frozen is a magnet's fringe field.

11. The method of claim 1, wherein the compound is a compound of biological relevance.

12. The method of claim 11, wherein the compound of biological relevance is chosen from the group consisting of acetic acid, acetate salts, pyruvate salts, and ethanol.

13. The method of claim 12, wherein the compound is 1-$^{13}$C—AcH (acetic acid), Na-1-$^{13}$C-acetate, or 2-$^{13}$C—EtOH (ethanol).

14. The method of claim 13, wherein the compound is 1-$^{13}$C—AcH.

15. A method for mixing a test sample having one or more hydrogen-containing $^{13}$C compound(s) and subsequently analyzing the test sample comprising the following steps performed in the indicated order:
   (a) mixing a composition containing one or more compound(s) comprising hydrogen and $^{13}$C with hyperpolarized $^{129}$Xe;
   (b) applying a magnetic field to the resulting mixture;
   (c) freezing the mixture;
   (d) reducing the magnetic field strength sufficiently so that spin polarization is transferred from the hyperpolarized $^{129}$Xe to the compound(s) within the frozen mixture by increasing the field strength of a separate electromagnet that compensates the existing magnetic field;
   (e) increasing the magnetic field strength by decreasing the field strength of said electromagnet;
   (f) thawing the mixture to obtain a test sample;
   (g) applying a $^{13}$C nuclear magnetic resonance (NMR) pulse sequence to the test sample; and
   (h) detecting the $^{13}$C active nuclei in the test sample by NMR spectroscopy, magnetic resonance imaging (MRI), or both.

16. The method of claim 15, wherein the one or more compound(s) comprising hydrogen and $^{13}$C are compounds of biological relevance and that have low solubility in liquid xenon.

17. The method of claim 15, wherein the step of thawing the mixture to obtain the test sample further comprises the step of exposing the mixture to other substances to obtain the test sample.

18. The method of claim 1, wherein the compound is in the form of a liquid.

* * * * *